United States Patent [19]

Beard, Jr. et al.

[11] Patent Number: 4,463,200

[45] Date of Patent: Jul. 31, 1984

[54] PROCESS FOR THE PRODUCTION OF PERCHLOROETHYLENE BY CATALYTIC OXYCHLORINATION

[75] Inventors: William O. Beard, Jr.; Charles R. Cupit, both of Wichita, Kans.; Patricia H. Moyer, Phoenix, Ariz.

[73] Assignee: Vulcan Materials Company, Birmingham, Ala.

[21] Appl. No.: 56,346

[22] Filed: Jul. 10, 1979

Related U.S. Application Data

[63] Continuation-in-part of Ser. No. 968,788, Dec. 12, 1978, , which is a continuation of Ser. No. 831,188, Sep. 7, 1977, abandoned.

[51] Int. Cl.$^3$ .............................................. C07C 21/12
[52] U.S. Cl. ................................................... 570/224
[58] Field of Search ..................... 260/654 A; 570/224

[56] References Cited

U.S. PATENT DOCUMENTS

| | | | |
|---|---|---|---|
| 3,232,889 | 2/1966 | Bellis | 260/659 A |
| 3,267,160 | 8/1966 | McGrewy et al. | 260/654 A |
| 3,468,968 | 9/1969 | Baker et al. | 260/659 A |
| 3,709,950 | 1/1973 | Baker et al. | 260/659 A |
| 3,926,847 | 12/1975 | Beard et al. | 260/654 A |
| 4,123,467 | 10/1978 | Campbell et al. | 260/654 A |

FOREIGN PATENT DOCUMENTS 1276026 8/1968 Fed. Rep. of Germany ... 260/654 A

Primary Examiner—Charles F. Warren
Assistant Examiner—Joseph A. Boska
Attorney, Agent, or Firm—Burns, Doane, Swecker and Mathis

[57] ABSTRACT

The production of undesirable 1,1,2-trichloroethane and unsym-tetrachloroethane during the production of perchloroethylene is eliminated or essentially eliminated by an improved oxychlorination reaction. The oxychlorination reaction is carried out in the presence of a copper chloride-alkali metal chloride catalyst mixture deposited on a microspheroidal activated alumina carrier having an average particle size of between about 40 and about 70 microns and a surface area of at least about 100 m$^2$/g with the copper chloride and alkali metal chloride being present on the carrier in a weight ratio of at least about 1.2 to 1. Reaction parameters, including, e.g., time, temperature and pressure, are controlled to produce a reaction product containing perchloroethylene and trichloroethylene, and the reaction product is free from 1,1,2-trichloroethane and unsym-tetrachloroethane.

12 Claims, No Drawings

PROCESS FOR THE PRODUCTION OF PERCHLOROETHYLENE BY CATALYTIC OXYCHLORINATION

CROSS-REFERENCES TO RELATED APPLICATIONS

This application is a continuation-in-part application of U.S. application Ser. No. 968,788, filed Dec. 12, 1978, which is a continuation of U.S. application Ser. No. 831,188, filed Sept. 7, 1977, now abandoned.

BACKGROUND OF THE INVENTION

1. Field of the Invention

This invention relates to improved processes for the production of perchloroethylene by catalytic oxychlorination.

2. General Background and Summary of the Prior Art

Perchloroethylene is a highly useful chlorinated hydrocarbon which is used primarily for dry cleaning of fabrics and for solvent degreasing of metal parts. The usage of other chlorinated hydrocarbons such as trichloroethylene is expected to decline in view of antipollution regulations such as the Federal Clean Air Act of 1970, which categorizes certain chlorinated hydrocarbons such as trichloroethylene as photochemically reactive substances, contributing to air pollution, and hence subject to severe emission restrictions. On the other hand, perchloroethylene, a highly chlorinated hydrocarbon containing no hydrogen, is specifically exempted from such restrictions.

In the prior art, both fixed bed and fluidized bed catalyst systems have been employed for oxychlorination reactions to produce perchloroethylene. Typical of catalysts used in fixed bed systems are those comprising a metal having a variable valence, such as copper, supported on a carrier. Fixed catalyst beds have the drawback, however, of tending to develop hot spots with the consequent deterioration of the catalyst, and with attendant loss of active material, heat transfer problems and catalyst recovery requirements. Accordingly, a more recent trend has been toward the utilization of fluidized catalyst beds which permit better control of the reaction which is exothermic, corrosive and even explosive, while at the same time eliminating hot spot formation.

One type of oxychlorination catalyst which has been utilized commercially in fluidized form comprises a mixture of copper chloride and potassium chloride deposited on a carrier of "Florex", a highly calcined Fullers' earth, which is essentially a magnesium-aluminum silicate with minor proportions of iron, calcium, potassium and titanium oxides. The resulting catalyst contains between 6% and 12% copper by weight. A catalyst of this kind is described, for example, in U.S. Pat. Nos. 3,267,162 and 3,296,319.

One major drawback of the known oxychlorination processes for producing perchloroethylene is that 1,1,2-trichloroethane and/or unsym-tetrachloroethane are by-products. See, for example, U.S. Pat. Nos. 3,267,160, 3,393,132, 3,468,968, 3,709,950 and 3,926,847. These by-products make separation of the principal product, perchloroethylene, much more difficult as can be seen from the respective boiling points,

|  | B.P. °C., Atm. Press. |
| --- | --- |
| trichloroethylene | 86.7 |
| 1,1,2-trichloroethane | 113.9 |
| perchloroethylene | 120.8 |
| unsym-tetrachloroethane | 130.5 |
| sym-tetrachloroethane | 145.9 |

Thus, there is only a 7° C. difference in boiling point between perchloroethylene and 1,1,2-trichloroethane. When 1,1,2-trichloroethane is absent, the boiling point difference to the next lower boiling compound from which it would have to be separated is 34° C. to the 86.7° C. boiling point of trichloroethylene. Similarly, there is only a 10° C. difference between perchloroethylene and unsym-tetrachloroethane. When unsym-tetrachloroethane is absent, there is a 25° C. difference to the 145° C. boiling point of sym-tetrachloroethane making its separation much less difficult.

Another drawback of most known oxychlorination processes is the presence of unacceptably high impurity levels in the perchloroethylene produced. For example, in the production of fluorocarbons, impurity levels must often be reduced to less than 50 parts per million. (See, for example, U.S. Pat. No. 3,751,494, which discloses a molecular sieve decontamination process to reduce impurity content). Such reductions of impurity levels are generally expensive and time-consuming processes.

A further drawback of most known oxychlorination processes is the strong tendency of hydrogen-containing impurities such as 1,1,1,2-tetrachloroethane to dehydrochlorinate at elevated temperatures. In the presence of metal surfaces, such as are generally found in chemical process equipment, these impurities or contaminants dehydrochlorinate releasing corrosive hydrochloric acid vapor (see, for example, U.S. Pat. No. 3,712,869). Similarly, 1,1,1,2-tetrachloroethane tends to undesirably decompose when subjected to operations such as distillation, rectification, evaporation or concentration.

The presence of acidic decomposition products has been recognized to be undesirable and deleterious in numerous patents dealing with dry cleaning and solvent degreasing applications employing perchloroethylene and the use of certain stabilizer systems primarily to counteract such acidic decomposition products (see, for example, U.S. Pat. No. 3,029,298).

Another drawback of most known oxychlorination processes is the toxicity level of saturated partially chlorinated hydrocarbon reaction products such as 1,1,2-trichloroethane and 1,1,1,2-tetrachloroethane as compared to perchloroethylene, (see "Threshold Limit Values, Chemical Substances in Workroom Air", published in National Safety News, October, 1974, pp. 95–104). Reduction in the levels of these impurities is desirable to minimize the potential of adverse effects resulting from repeated exposure of workers to such chemicals when the workers are involved in processes for producing or in processes which utilize the chemicals.

Yet another drawback of most known oxychlorination catalysts of the prior art is that it has not been possible simultaneously to obtain both a high yield of perchloroethylene in relation to carbon content of the feed, and good utilization of chlorine, whether furnished as HCl or chlorine or both. These known catalysts bring about the formation of substantial quantities of trichloroethylene, usually such that the mole ratio of perchloroethylene to trichloroethylene, under conditions that would give good chlorine utilization, is less than 3:1. Higher perchloroethylene to trichloroethylene mole ratios are typically obtained only at chlorine utilization as low as about 70%.

Experience has also shown that oxychlorination catalysts of the type described exhibit the undesired phenomenon of slugging. This abnormality in fluidization is a condition which has been described as one in which bubbles of gas coalesce to a size approaching the order of magnitude of the confining vessel. The particle layers, or slugs of granular solids, between such large gas bubbles, move upward in a piston-like manner, reaching a certain height, and then disintegrate, with the result that the catalyst rains down as individual particles or smaller aggregates. Slugging is undesirable from a purely mechanical standpoint in that stresses are produced in the reactor arising from shaking of the vessel. Moreover, the size of the reactor is limited owing to the unpredictability of the slugging phenomenon, which sometimes requires that the reactor be placed within a coolant bath consisting of a larger vessel, as described, for example, in British Pat. No. 1,123,477.

In most known oxychlorination processes, the reduction of the level of undesired by-products such as 1,1,2-trichloroethane or unsym-tetrachloroethane is accomplished by complex and costly post-oxychlorination procedures such as filtration, distillation, or recycle. See, for example, U.S. Pat. No. 3,751,494.

Other drawbacks of known oxychlorination processes have been recognized. For example, Fichtel et al, German patent specification No. 1,276,026, deals with oxychlorination processes requiring complex and costly distillation and recycle procedures to separate reactants which have not been converted in the oxychlorination reaction. Even with such procedures, however, such prior art processes result in the production of high levels of trichloroethylene (which as discussed herein, is undersirable) as well as the production of unacceptably high levels of undesirable chlorinated by-products.

SUMMARY OF THE INVENTION

Accordingly, a primary object of the present invention is to provide an improved oxychlorination process for the production of perchloroethylene, which process does not incur or which substantially alleviates the above-discussed disadvantages and problems of the prior art.

Another object of the present invention is to provide an improved process for the production of perchloroethylene by catalytic oxychlorination which process, without separation, recycle, purification or any other post-oxychlorination process step, produces no or essentially no undesirable 1,1,2-trichloroethane or unsym-tetrachloroethane.

Another object of the present invention is to provide an improved catalytic oxychlorination process for the production of perchloroethylene at relatively high ratios of perchloroethylene to less desirable trichloroethylene.

Yet another object of the present invention is to provide an improved process for the production of perchloroethylene by catalytic oxychlorination whereby satisfactory perchloroethylene selectivity as well as a high level of chlorine utilization are achieved.

Yet another object of the present invention is to provide an improved process for the production of perchloroethylene, which process does not incur or which substantially alleviates the problems of hot spot formation and slugging in a catalyst bed system.

In accordance with one aspect of the present invention, an improvement is provided in the production of perchloroethylene by oxychlorination of at least one $C_2$ hydrocarbon using a copper chloride-alkali metal chloride catalyst mixture deposited on a carrier, which improvement comprises carrying out the oxychlorination reaction at a temperature and for a time sufficient to produce a reaction product containing less than about 150 ppm each on a perchloroethylene weight basis of 1,1,2-trichloroethane and unsym-tetrachloroethane, where activated alumina having an average particle size of between about 40 and about 70 microns and a surface area of at least about 100 $m^2/g$ is used as the carrier for the copper chloride-alkali metal chloride catalyst mixture, the copper chloride and alkali metal chloride being present in a weight ratio of above about 1.2:1, the copper chloride calculated as $CuCl_2$.

In accordance with another aspect of the present invention, an improved process for the production of perchloroethylene is provided, which process comprises oxychlorinating at least one partially chlorinated $C_2$ hydrocarbon with (a) above about 75% of a stoichiometric amount of at least one member selected from the group consisting of hydrogen chloride and chlorine and (b) at least one member selected from the group consisting of oxygen and oxygen-containing gases with oxygen being present during oxychlorination at above stoichiometric amounts, the oxychlorination reaction being carried out at a temperature of between about 370° C. and about 450° C. and at a pressure of between about 1 atmosphere and about 15 atmospheres, the oxychlorination reaction being conducted in the presence of a supported catalyst consisting essentially of copper chloride and potassium chloride on a microspheroidal activated alumina support having an average particle size of between about 40 and about 70 microns and a surface area of from about 100 $m^2/g$ to about 250 $m^2/g$, the copper chloride and potassium chloride being present in a weight ratio of between about 5:1 and about 1.2:1, the copper chloride calculated as $CuCl_2$, and together comprising from about 20% to about 40% by weight of the supported catalyst, and the reaction being carried out at a mole ratio of member (a) to partially chlorinated $C_2$ hydrocarbon and for a time sufficient to produce a reaction product containing perchloroethylene and trichloroethylene at a mole ratio above about 5:1, and wherein the reaction product contains less than about 150 ppm each on a perchloroethylene weight basis of 1,1,2-trichloroethane and unsym-tetrachloroethane, while still reacting above about 75 weight percent of member (a).

In yet another aspect of the present invention, an improved catalytic oxychlorination process for the production of perchloroethylene is provided, which process comprises passing ethylene dichloride and above about 75% of a stoichiometric amount of chlorine or hydrogen chloride and more than a stoichiometric amount of oxygen into a reaction zone containing a fluidized bed consisting essentially of a supported catalyst in a particulate fluidizable form, the supported catalyst consisting essentially of a catalytic amount of copper chloride and alkali metal chloride impregnated on a microspheroidal activated alumina support having an average particle size of between about 40 and about 70 microns and a surface area of at least about 100 $m^2/g$, the weight ratio of copper chloride to alkali metal chloride being above about 1.2:1, the copper chloride calculated as $CuCl_2$, and maintaining a superficial linear velocity of the ethylene dichloride, hydrogen chloride or chlorine, and oxygen or oxygen-containing gas fed into the reaction zone above minimum fluidization velocity for the bed and a reaction zone temperature between about 370° C. and about 450° C. and a reaction zone pressure between about 1 atmosphere and about 15 atmospheres for a superficial reaction zone residence time of between about 5 seconds and about 30 seconds and at a mole ratio of hydrogen chloride or chlorine to ethylene dichloride sufficient to produce a reaction product containing perchloroethylene and trichloroethylene at a mole ratio of above about 5:1 with the reaction product containing less than about 150 ppm each on a perchloroethylene weight basis of 1,1,2-trichloroethane and unsym-tetrachloroethane, while still reacting above about 75 weight percent of the hydrogen chloride or chlorine.

In a highly preferred aspect of the present invention, an improved catalytic oxychlorination process for the production of perchloroethylene is provided, which process comprises passing reactants consisting essentially of ethylene dichloride and hydrogen chloride with a mole ratio of hydrogen chloride to ethylene dichloride above about 1.6, and at least one member selected from the group consisting of oxygen and oxygen-containing gases, into a reaction zone with oxygen being present at about 20% to about 35% in excess of stoichiometric, the reaction zone containing a fluidized bed consisting essentially of a supported catalyst in particulate fluidizable form, the supported catalyst consisting essentially of a catalyst mixture of copper chloride and potassium chloride impregnated on a microspheroidal activated alumina support having an average particle size of about 60 microns and a surface area of between about 150 m²/g and about 250 m²/g, the catalyst mixture comprising from about 25% to about 30% of the supported catalyst, and the weight ratio of copper chloride to potassium chloride being between about 2:1 and about 1.2:1, the copper chloride calculated as CuCl₂, and maintaining a superficial linear velocity of the ethylene dichloride and other reactants fed into the reaction zone above minimum fluidization velocity for the bed and at a reaction zone temperature of between about 400° C. and about 430° C. and at a reaction zone pressure of between about 1 atmosphere and about 6 atmospheres for a superficial reaction zone residence time of between about 10 seconds and about 20 seconds and sufficient to produce a reaction product containing perchloroethylene and trichloroethylene at a ratio of above about 5:1 with the reaction product containing less than about 150 ppm each and preferably less than about 10 ppm each on a perchloroethylene weight basis of 1,1,2-trichloroethane or unsym-tetrachloroethane, while still reacting above about 75 weight percent of the hydrogen chloride.

Other objects, aspects and advantages of the present invention will become apparent to one skilled in the art from the following description of the preferred embodiments.

DESCRIPTION OF THE PREFERRED EMBODIMENTS

Perchloroethylene may be produced by catalytically oxychlorinating at least one $C_2$ hydrocarbon or an incompletely chlorinated derivative thereof. Preferably, in accordance with the present invention, perchloroethylene is produced by catalytically oxychlorinating at least one incompletely chlorinated $C_2$ aliphatic hydrocarbon derivative, e.g., ethyl chloride (chloroethane), 1,1-dichloroethane, 1,1,2-trichloroethane, cis- and trans-dichloroethylene, and ethylene dichloride (1,2-dichloroethane). Ethylene dichloride is most preferred. Mixtures of the above $C_2$ hydrocarbons, their incompletely chlorinated derivatives, or mixtures thereof may also be used. As used herein, the term "$C_2$ hydrocarbon" shall include $C_2$ hydrocarbons, their incompletely chlorinated derivatives, and mixtures thereof.

The stoichiometric amount of a partially chlorinated $C_2$ hydrocarbon of the formula $C_2H_{6-a}Cl_a$ or $C_2H_{4-b}Cl_b$ may be defined as:

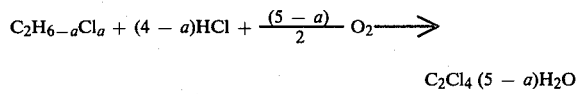
$$C_2H_{6-a}Cl_a + (4 - a)HCl + \frac{(5 - a)}{2} O_2 \longrightarrow$$
$$C_2Cl_4 (5 - a)H_2O$$

or

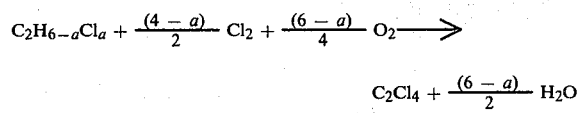
$$C_2H_{6-a}Cl_a + \frac{(4 - a)}{2} Cl_2 + \frac{(6 - a)}{4} O_2 \longrightarrow$$
$$C_2Cl_4 + \frac{(6 - a)}{2} H_2O$$

and

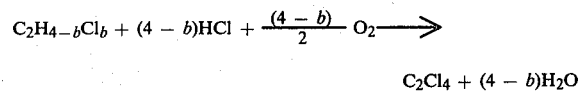
$$C_2H_{4-b}Cl_b + (4 - b)HCl + \frac{(4 - b)}{2} O_2 \longrightarrow$$
$$C_2Cl_4 + (4 - b)H_2O$$

or

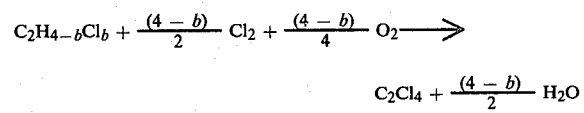
$$C_2H_{4-b}Cl_b + \frac{(4 - b)}{2} Cl_2 + \frac{(4 - b)}{4} O_2 \longrightarrow$$
$$C_2Cl_4 + \frac{(4 - b)}{2} H_2O$$

Where a or b is the number of chlorine atoms in the partially chlorinated $C_2$ hydrocarbon.

When perchloroethylene is produced from ethylene dichloride by catalytic oxychlorination with hydrogen chloride or chlorine and oxygen or oxygen-containing gas, there is formed, besides perchloroethylene, trichloroethylene. The respective reactions may be presented by the equations:

(I)
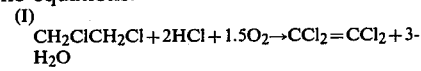
$$CH_2ClCH_2Cl + 2HCl + 1.5O_2 \rightarrow CCl_2=CCl_2 + 3H_2O$$

or

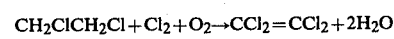
$$CH_2ClCH_2Cl + Cl_2 + O_2 \rightarrow CCl_2=CCl_2 + 2H_2O$$

and (II)
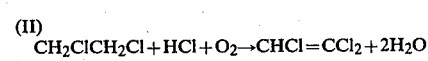
$$CH_2ClCH_2Cl + HCl + O_2 \rightarrow CHCl=CCl_2 + 2H_2O$$

or

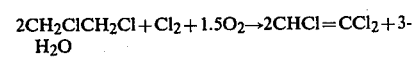
$$2CH_2ClCH_2Cl + Cl_2 + 1.5O_2 \rightarrow 2CHCl=CCl_2 + 3H_2O$$

Also, during oxychlorination of ethylene dichloride to perchloroethylene, there is typically formed, besides perchloroethylene and trichloroethylene, some lower boiling compounds and some higher boiling compounds, as well as some carbon monoxide and carbon dioxide. Lower boiling compounds typically include vinyl chloride, ethyl chloride, vinylidene chloride, trans- and cis-dichloroethylene and carbon tetrachloride. Higher boiling compounds typically include sym-tetrachloroethane, pentachloroethane and hexachloroethane. Traces of hexachlorobutadiene and hexachlorobenzene may also be present. As indicated above, the undesirable 1,1,2-trichloroethane and unsym-tetrachloroethane are in accordance with the present invention not present in the reaction product at all or are present in very insignificant amounts only, e.g., less than about 150 ppm of each compound on a perchloroethylene weight basis and preferably less than about 10 ppm of each compound on a perchloroethylene weight basis. Further, the mole ratio of perchloroethylene to trichloroethylene is typically above about 5:1. Further, the total chlorinated by-products formed, in relation to the total yield of perchloroethylene and trichloroethylene, ordinarily does not exceed about 10% and desirably is significantly less.

The incompletely chlorinated $C_2$ aliphatic hydrocarbon derivatives such as ethylene dichloride or other starting material may be reacted in any convenient physical form. For example, ethylene dichloride may be vaporized and mixed with oxygen or oxygen-containing gas in the reaction zone. Instead of vaporization the starting material may be introduced into the reaction zone as a liquid in the form of, for example, droplets, mists or atomized jet. If necessary, any starting material which is normally solid at ambient temperatures or which sublimes upon heating may be dissolved in a liquid chlorocarbon prior to introduction into the reaction zone or may be introduced into the reaction zone as a slurry or as a solid.

Perchloroethylene may be produced by catalytic oxychlorination at a wide variety of temperatures and pressures. For example, an incompletely chlorinated $C_2$ hydrocarbon derivative such as ethylene dichloride may be oxychlorinated with hydrogen chloride or chlorine and oxygen or an oxygen-containing gas at reaction temperatures of between about 350° C. and about 475° C., more typically between about 370° C. and about 450° C., and preferably between about 400° C. and about 430° C.

Atmospheric, subatmospheric or superatmospheric reaction pressures may be employed. The reaction pressures typically may vary from about 1 atmosphere (absolute) to about 20 atmospheres (absolute), more typically from about 1 atmosphere (absolute) to about 15 atmospheres (absolute), and preferably from about 1 atmosphere (absolute) to about 6 atmospheres (absolute).

The oxychlorination reaction is typically conducted for a time sufficient to produce a substantial amount of perchloroethylene, e.g., above about 70% and preferably above about 75%, of perchloroethylene based on carbon utilization, with a mole ratio of perchloroethylene to trichloroethylene being above about 5:1. For example, the superficial reaction zone residence times may be from several seconds or several minutes, e.g., from about 2 seconds up to about 1 minute, and preferably from about 5 seconds up to about 30 seconds, and most preferably from about 10 seconds up to about 20 seconds.

Oxygen may be supplied for the reaction in the form of pure oxygen gas or as an oxygen-containing gas such as air. The ratio of total feed of oxygen to total feed of organic starting material is a variable number which depends upon the specific composition of the feed and other process design factors. The oxychlorination reaction may be conducted with an amount of oxygen that varies from above about the stoichiometric amount required to completely oxychlorinate the organic compound to perchloroethylene, plus any contained hydrogen to water, and more typically is from above about stoichiometric to about 200% in excess of this amount, preferably from about 10 to about 50% in excess, and most preferably from about 20 to about 35% in excess of stoichiometric.

For the oxychlorination reaction, hydrogen chloride or chlorine or both are also supplied to the reaction zone. The ratio of total feed of chlorine and/or hydrogen chloride to total feed of organic starting material again is a variable number which depends upon the specific composition of the feed and other process design factors. The oxychlorination reaction is typically conducted with an amount of chlorine and/or hydrogen chloride that varies from above about 75% of the stoichiometric amount required to oxychlorinate completely the organic starting material to perchloroethylene. For example, it is most preferred when ethylene dichloride is being catalytically oxychlorinated to perchloroethylene to maintain a mole ratio of hydrogen chloride to ethylene dichloride of above about 1.6, e.g., from between about 1.6 to about 1.9.

As indicated above, the process of the present invention is conducted in the presence of a copper chloride-alkali metal chloride catalyst mixture deposited on a specific carrier or support. The alkali metal chloride may be potassium, sodium or lithium chloride. A preferred catalyst mixture is one comprising cupric chloride and potassium chloride. Cuprous chloride may also be used, insofar as in an oxidizing environment cuprous chloride is readily converted to cupric chloride.

It has been found, surprising and unexpectedly, that when the copper chloride-alkali metal chloride catalyst mixture is deposited on a microspheroidal activated alumina support or carrier having an average particle size of between about 40 and about 70 microns and a surface area of at least about 100 $m^2/g$, and when the reaction is carried out at a sufficient temperature and for a sufficient time as discussed above, the result is to bring about elimination or a significant reduction in the amount of undesirable 1,1,2-trichloroethane or unsym-tetrachloroethane produced. Further, a high mole ratio of perchloroethylene to trichloroethane is also maintained under conditions that ordinarily would be expected to produce relatively large amounts of incompletely chlorinated hydrocarbons such as trichloroethylene. In addition, the supported catalysts according to the present invention make it possible to achieve high perchloroethylene yields simultaneously with excellent chlorine utilization. Thus, in accordance with the present invention, perchloroethylene yields of about 75% or more are readily obtainable, while still utilizing or reacting above about 75% of the chlorine employed.

The preferred microsperiodal activated alumina supports have an average particle size of between about 50 and about 60 microns and a surface area of at least about 100 $m^2/g$ and most preferably between about 150 $m^2/g$ and about 250 $m^2/g$.

The copper chloride-alkali metal chloride catalyst mixture may be deposited or impregnated on the carrier or support in accordance with conventional procedures. Thus, a solution, slurry or paste of the copper chloride-alkali metal chloride catalyst mixture may be applied to the carrier by spraying, immersion or the like.

The amount of copper chloride and alkali metal chloride salts used is such that the supported catalyst product contains a catalytically effective amount of the active metal salts. For example, the catalyst mixture may comprise between about 20% and about 40%, by weight, and preferably between about 25% and about 30%, by weight, of the total of the catalyst mixture and the carrier. The percent by weight is based upon the total weight of the metal chlorides and the carrier. The weight ratio of copper chloride to alkali metal chloride may vary depending upon the type of feed and other process conditions. For example, the weight ratio of copper chloride to alkali metal chloride may be between about 5:1 and about 1.2:1, and more preferably between about 2:1 and about 1.2:1, e.g., about 3:2. In calculating the weight ratio of copper chloride to alkali metal chloride, the copper chloride is calculated as cupric chloride ($CuCl_2$). Thus, by the use of the term "calculated as $CuCl_2$" in the specification and claims herein, it is meant that where cupric chloride ($CuCl_2$) is employed in the catalyst mixture, e.g., to obtain a copper chloride to alkali metal chloride ratio of 1.2:1, 1.2 grams of cupric chloride are employed per gram of alkali metal chloride and where cuprous chloride (CuCl) is employed in the catalyst mixture, e.g., to obtain the same copper chloride to alkali metal chloride ratio (i.e., 1.2:1 in the above example), enough cuprous chloride must be employed so that, upon conversion of the cuprous chloride to cupric chloride, 1.2 grams of reacted cupric chloride will be present per gram of alkali metal chloride.

While the process of the present invention may be carried out in fixed bed or fluidized bed, the process of the present invention is preferably performed utilizing a fluidized bed of the supported catalyst in fluidizable form.

When the supported catalyst is present in a fluidized or fixed bed, minor amounts of other inert particulate matter, e.g., Fuller's earth, pumice and ceramic material, may be mixed therewith.

Perchloroethylene and any trichloroethylene may be recovered from the reaction product stream by any suitable technique known to those skilled in the art. Thus, the effluent from the reactor may be passed through a cooler and a condensor to a phase separator which collects the condensed chlorohydrocarbons and the hydrochloric acid. The chlorocarbon stream from the phase separator may then be neutralized, dried and sent to a fractional distillation system for perchloroethylene and trichloroethylene purification.

However, it should be noted that the reaction product of the oxychlorination process of this invention, prior to any separation, purification, recycle, or any other post-oxychlorination process step, contains less than about 150 ppm each, and preferably less than about 10 ppm each, based on a perchloroethylene weight basis, of 1,1,2-trichloroethane and unsym-tetrachloroethane. Thus, as used in the specification and claims herein, the term "reaction product" means the reaction product of the oxychlorination reaction prior to any separation, purification, recycle, or any other post-oxychlorination process step, and particularly any other step involving, e.g., recycle, separation, purification or reaction of any undesirable by-products.

The present invention is additionally illustrated but not limited by the following examples; all parts, percentages and ratios indicated herein are by weight unless otherwise specified.

EXAMPLE I

For this series of runs a copper chloride-potassium chloride catalyst on a microspheroidal activated alumina support (A) was prepared for use in accordance with the present invention, and six copper chloride-potassium chloride catalysts on other types of supports (B to G), outside the scope of the present invention were prepared for comparison purposes. Each of these supported catalysts was then used for catalytic oxychlorination of ethylene dichloride.

Preparation of Catalyst 2,722 grams of the powdered catalyst support was spread on a pan. An aqueous solution of 690 grams of cupric chloride dihydrate and 363 grams of potassium chloride in a total volume of 1400 milliliters was sprinkled over the powdered catalyst support as evenly as possible in portions followed by thorough manual mixing each time. All the solution was taken up by the solid. The mixture was then spread out to dry under heat lamps with frequent stirring and mixing to break up lumps and finally dried at 220° C. for two hours in an oven. This catalyst contained 15.54 weight percent copper chloride and 10.32 weight percent potassium chloride as shown by analysis. Target loadings for this catalyst were 15.0 and 10.0 weight percent copper chloride and potassium chloride, respectively, as calculated by the total weight of anydrous metal chlorides and the carrier.

Table IA presents data on types and amounts of carriers and solids used.

TABLE IA

Preparation of Various Supported Catalysts

| | Catalyst Support | Surface Area ($m^2/g$) | Approx. Average Particle Size (microns) | Weight $CuCl_2$ | Percent KCl |
|---|---|---|---|---|---|
| A | Microspheroidal activated alumina | 190 | 60 | 15.0 | 10.0 |
| B | Silica-alumina | 150 | 60 | 18.0 | 12.0 |
| C | Silica-gel | 600 | 60 | 15.0 | 10.0 |
| D | Silica-gel | 350 | 60 | 18.0 | 12.0 |
| E | Zeolite-containing fluidizable cracking catalyst | 180 | 85 | 18.0 | 12.0 |
| F | Microspheroidal alumino-silicate/ smectite-illite layered | 180 | 75 | 16.6 | 11.0 |
| G | Calcined Fuller's earth | 130 | 175 | 18.0 | 12.0 |

Catalytic Oxychlorination in Fluidized Bed

The catalytic oxychlorinations where run in a fluidized bed unit having a reaction zone 2 inches in diameter and 13 feet in height and an expansion zone 6 inches in diameter and 2 feet in height. The reactor was provided with a movable thermocouple within a central thermowell which extended from the top to within 3 inches of the bottom of the bed. Vaporized 1,2-dichloroethane was mixed at a tee with air and HCl or $Cl_2$. The feeds were then led through a ¼-inch tube 6 inches in length to a cone-shaped inlet which was flanged onto the reaction zone of the fluid bed. The reaction zone was provided with an electrically heated jacket containing Dowtherm A, a product of The Dow Chemical Co., the pressure of which was adjusted in order to regulate the temperature within the bed.

For a typical run, reactor was charged with sufficient catalyst to provide a bed height of approximately 7 feet. The bed was fluidized with nitrogen at atmospheric pressure and preheated to a temperature about 50° to 70° F. below the desired operating temperature. Feeds were then substituted for the nitrogen flow and the pressure adjusted to the desired value by means of a back-pressure regulator. A superficial velocity of 0.6 feet per second was usually employed.

Typical results obtained with catalysts of this invention and other catalysts outside the scope of the present invention appear in Tables IB, II, III and IV.

perchloroethylene. The amount of oxygen required per mole of HCl in the feed is 1 mole in making trichloroethylene, Equation (1), and 0.75 moles for making perchloroethylene, Equation (2). It may be derived from the equations that if mole ratio, r, of HCl to EDC in the feed is between 1 and 2, then (3) $x = 2 - r$ where x is the moles of trichloroethylene formed per mole of EDC fed.

(4) $y = r - 1$ where y is the moles of perchloroethylene formed per mole of EDC fed.

(5) $T = 0.5 + 0.5 \, r$ where T is the theoretical moles of oxygen required per mole of EDC fed [Eq. (1) & (2)] for any given HCl/EDC mole ratio, r.

As may be seen from the above Tables IA and IB, run

TABLE IB

| Catalytic Oxychlorination of Ethylene Dichloride to Perchloroethylene | | | | | | | |
|---|---|---|---|---|---|---|---|
| Run Series No. | 1 | 2 | 3 | 4 | 5 | 6 | 7 |
| Catalyst | A | B | C | D | E | F | G |
| Mole Ratio $O_2$:EDC | 1.68 | 1.80 | 1.70 | 1.75 | 1.70 | 1.67 | 1.61 |
| Mole Ratio HCl:EDC | 1.66 | 1.68 | 1.64 | 1.70 | 1.65 | 1.65 | 1.73 |
| Excess $O_2$, % | 26.1 | 34.1 | 31.5 | 28.0 | 28.1 | 25.5 | 17.9 |
| Temperature, °C. | 413 | 420 | 422 | 418 | 427 | 424 | 404 |
| Linear Velocity, feet per second | 0.62 | 0.61 | 0.63 | 0.57 | 0.58 | 0.62 | 0.54 |
| Average pressure, atms. (absolute) | 5.0 | 5.3 | 5.0 | 5.2 | 5.3 | 5.1 | 5.0 |
| HCl Conversion, % | 80.2 | 84.9 | 86.9 | 86.7 | 87.0 | 86.4 | 76.3 |
| EDC Selectivity to Perchloroethylene, % | 76.8 | 63.6 | 52.0 | 43.9 | 69.9 | 68.0 | 56.8 |
| EDC Selectivity to Trichloroethylene, % | 4.6 | 13.2 | 19.5 | 20.1 | 10.6 | 12.7 | 20.9 |
| EDC Selectivity to ($CO_2$ + CO), % | 15.2 | 14.8 | 16.0 | 20.1 | 13.4 | 13.7 | 14.3 |
| EDC Selectivity to 1,1,2-trichloroethane, % | .000 | .000 | .000 | .000 | .000 | .000 | .000 |
| EDC Selectivity to Unsym-tetrachloroethane, % | .000 | .328 | .019 | .042 | .038 | .100 | .192 |

Run Series 6 is typical of the catalytic oxychlorination process of U.S. Pat. No. 3,926,847. Run Series 2-4 and 7 are typical of the catalytic oxychlorination process of U.S. Pat. No. 3,267,160.

The theoretical amount of oxygen required for a given mole ratio of HCl to EDC in the feed may be derived from the equations for the oxychlorination of EDC to trichloroethylene and to perchloroethylene.

(1)

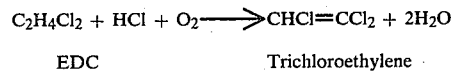

EDC           Trichloroethylene (2)

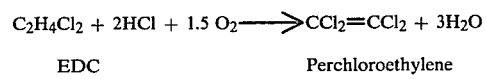

EDC           Perchloroethylene

These equations show that the mole ratio of HCl to EDC is 1 for making trichloroethylene and 2 for making series 1, corresponding to the present improved oxychlorination process and using the copper chloride-potassium chloride catalyst on a microspheroidal activated alumina support of the most preferred surface area and particle size resulted in the production of perchloroethylene at a high ratio of perchloroethylene to trichloroethylene, with no production of 1,1,2-trichloroethane or unsym-tetrachloroethane, and at high HCl conversion rates.

Although several of the catalysts appearing in Tables IA and IB showed higher conversions, none were as successful in achieving as high perchloroethylene selectivity nor in achieving zero 1,1,1-tetrachloroethane as well as zero 1,1,2-trichloroethane selectivity.

EXAMPLE II

Run series 1 of Example 1 was repeated except that the amounts and ratios of copper chloride and potassium chloride were varied. Data and results appear in TABLE II.

TABLE II

| Comparison of Various $CuCl_2$/KCl Ratios with High Surface area Microspheroidal Activated Alumina as the Catalyst Support | | | | | | | | | | | | |
|---|---|---|---|---|---|---|---|---|---|---|---|---|
| $CuCl_2$/ KCl Mole Ratio | Wt. Percent | | HCl/ EDC Mole Ratio | % Excess $O_2$ | Avg. Temp. °C. | Avg. Press. Atm. (abs) | SLV ft/sec | HCl Conv. | EDC Selectivity to (%) | | | |
| | $CuCl_2$ | KCl | | | | | | | Perc | TCE | $CO_2$ + CO | 1,1,2- | 1,1,1- |
| 0.61 | 12.0 | 10.9 | 1.58 | 36.0 | 414 | 5.0 | 0.62 | 71.5 | 57.3 | 16.3 | 18.8 | .004 | .480 |
| 0.83 | 15.0 | 10.0 | 1.66 | 26.1 | 413 | 5.0 | 0.62 | 80.2 | 76.8 | 4.6 | 15.2 | .000 | .000 |

TABLE II-continued

Comparison of Various CuCl$_2$/KCl Ratios with High Surface area Microspheroidal Activated Alumina as the Catalyst Support

| CuCl$_2$/KCl Mole Ratio | Wt. Percent CuCl$_2$ | Wt. Percent KCl | HCl/EDC Mole Ratio | % Excess O$_2$ | Avg. Temp. °C. | Avg. Press. Atm. (abs) | SLV ft/sec | HCl Conv. | EDC Selectivity to (%) Perc | TCE | CO$_2$ + CO | 1,1,2- | 1,1,1,2- |
|---|---|---|---|---|---|---|---|---|---|---|---|---|---|
| 1.10 | 18.0 | 9.0 | 1.68 | 30.2 | 420 | 5.5 | 0.56 | 80.3 | 77.8 | 1.9 | 16.7 | .000 | .000 |

Perc = Perchloroethylene
TCE = Trichloroethylene
1,1,2- = 1,1,2-trichloroethane
1,1,1,2- = unsym-tetrachloroethane As may be seen from Table II, best results are obtained when the copper chloride to potassium chloride weight ratio was above about 1.2. The results at the lower weight ratio of copper chloride to potassium chloride show reduced HCl conversions, less favorable perchloroethylene selectivity based upon carbon utilization, and the presence of a considerable amount of by-product 1,1,1,2-tetrachloroethane as well as poor perchloroethylene selectivity based upon carbon utilization.

EXAMPLE III

Run series 1 of Example 1 was repeated except that various total loadings of copper chloride and potassium chloride were used while maintaining a constant copper chloride to potassium chloride weight ratio. Data and results are shown below in Table III.

TABLE III

Comparison of CuCl$_2$ + KCl Loadings, with Constant CuCl$_2$/KCl Weight Ratio and with high surface area microspheroidal activated alumina as the Catalyst Support

| Wt. Percent CuCl$_2$ | Wt. Percent KCl | HCl/EDC Mole Ratio | % Excess O$_2$ | Avg. Temp. °C. | Avg. Press. Atm. (abs) | SLV ft/sec | HCl Conv. | Selectivity to Perc | TCE | CO + CO$_2$ | 1,1,2- | 1,1,1,2- |
|---|---|---|---|---|---|---|---|---|---|---|---|---|
| 10.0 | 6.7 | 1.64 | 29.6 | 415 | 4.9 | 0.64 | 74.1 | 70.3 | 8.9 | 16.8 | .000 | .104 |
| 15.0 | 10.0 | 1.66 | 16.1 | 413 | 5.0 | 0.62 | 80.2 | 76.8 | 4.6 | 15.2 | .000 | .000 |
| 18.0 | 12.0 | 1.61 | 31.0 | 415 | 5.5 | 0.49 | 88.3 | 74.1 | 5.2 | 23.2 | .000 | .000 |

As may be seen from Table III, total catalyst loading of about 16.7 weight percent, even at the excellent copper chloride to potassium chloride weight ratio of 1.5, may result in the production of some 1,1,1,2-tetrachloroethane. In addition, the 16.7 weight percent total catalyst loading resulted in poorer perchloroethylene selectivity as well as reduced overall HCl utilization.

EXAMPLE IV

Run series 1 of Example I was repeated except that the HCl/EDC mole feed ratio was varied. Data and results are shown in Table IV.

TABLE IV

Comparison of HCl/EDC Feed Mole Ratio for a 15 Wt % CuCl$_2$-10 Wt % KCl Catalyst Loading Microspheroidal Activated Alumina

| HCl/EDC Mole Ratio | % Excess O$_2$ | Avg. Temp. °C. | Avg. Press. Atm. (abs) | SLV ft/sec | HCl Conv. | Selectivity to Perc | TCE | CO + CO$_2$ | 1,1,2- | 1,1,1,2- |
|---|---|---|---|---|---|---|---|---|---|---|
| 1.38 | 36.2 | 414 | 5.1 | 0.57 | 82.4 | 56.8 | 22.0 | 17.3 | .000 | .108 |
| 1.66 | 26.1 | 413 | 5.0 | 0.62 | 80.2 | 76.8 | 4.6 | 15.2 | .000 | .000 |
| 1.85 | 32.6 | 414 | 5.1 | 0.62 | 76.7 | 80.1 | 1.1 | 15.5 | .000 | .000 |

Choice of an HCl to ethylene dichloride feed ratio below about 75 percent of the stoichiometric amount required to oxychlorinate completely the ethylene dichloride to perchloroethylene results in unfavorable by-product formation of 1,1,1,2-tetrachloroethane as well as poor perchloroethylene selectivity based upon carbon utilization.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the present invention.

We claim:

1. An improved process for the production of perchloroethylene by oxychlorination of at least one C$_2$ hydrocarbon, or an incompletely chlorinated derivative thereof, using a copper chloride-alkali metal chloride catalyst mixture deposited in a catalytically effective amount on a carrier, the carrier comprising microspheroidal activated alumina having an average particle size of between about 40 and about 70 microns and a surface area of at least about 100 m$^2$/g, the weight ratio of copper chloride to alkali metal chloride being above about 1.2:1, the copper chloride calculated as CuCl$_2$, and the reaction being carried out at a temperature and for a time sufficient to produce a reaction product containing perchloroethylene and trichloroethylene in a mole ratio of above about 5:1 and wherein the reaction product contains less than about 150 ppm each on a perchloroethylene weight basis of 1,1,2-trichloroethane and unsym-tetrachloroethane.

2. A process according to claim 1 wherein the oxychlorination is conducted at a temperature of between about 350° C. and about 475° C. at a pressure of between about 1 atmosphere and about 20 atmospheres, and for a time of between about 2 seconds and about 1 minute and wherein the oxchlorination is conducted in a reaction zone containing a fluidized bed consisting essentially of the catalyst mixture deposited on the microspheroidal activated alumina carrier.

3. A process according to claim 1 wherein ethylene dichloride is oxychlorinated to a reaction product containing less than about 10 ppm each on a perchoroethylene weight basis of 1,1,2,-trichloroethane and unsym-tetrachloroethane.

4. A process according to claim 1 wherein the alkali metal chloride is potassium chloride and the catalyst mixture comprises from about 20% by weight to about 40% by weight of the total weight of the catalyst mixture and the carrier.

5. An improved process for the production of perchloroethylene, which process comprises oxychlorinating at least one partially chlorinated $C_2$ hydrocarbon with (a) above about 75% of a stoichiometric amount of at least one member selected from the group consisting of hydrogen chloride and chlorine and (b) at least one member selected from the group consisting of oxygen and oxygen-containing gases with oxygen being present during oxychlorination at above stoichiometric amounts, the oxychlorination reaction being carried out at a temperature of between about 370° C. and about 450° C. and at a pressure of between about 1 atmosphere and about 15 atmospheres, the oxychlorination reaction being conducted in the presence of a supported catalyst consisting essentially of copper chloride and potassium chloride on a microspheroidal activated alumina support having an average particle size of between about 40 and about 70 microns and a surface area of from about 150 $m^2/g$ to about 250 $m^2/g$, the copper chloride and potassium chloride being present in a weight ratio of between about 5:1 and about 1.2:1, the copper chloride calculated as $CuCl_2$, and together comprising from about 20% by weight to about 40% by weight of the supported catalyst, the reaction being carried out at a mole ratio of member (a) to partially chlorinated $C_2$ hydrocarbon and for a time sufficient to produce a reaction product containing perchloroethylene and trichloroethylene at a mole ratio above about 5:1 and the reaction product containing less than about 150 ppm each on a perchloroethylene weight basis of 1,1,2-trichloroethane and unsym-tetrachloroethane, while still reacting above about 75 weight percent of member (a).

6. A process according to claim 5 wherein the partially chlorinated $C_2$ hydrocarbon is ethylene dichloride, and wherein member (a) is hydrogen chloride and the mole ratio of member (a) to ethylene dichloride is above about 1.6, and wherein the reaction product contains less than about 10 ppm each on a perchloroethylene weight basis of 1,1,2-trichloroethane and unsym-tetrachloroethane.

7. A process according to claim 5 wherein the reaction is conducted by passing reactants through a fluidized bed consisting essentially of the supported catalyst.

8. A process according to claim 5 wherein the oxychlorination reaction is conducted in the presence of oxygen at about 10 to about 50% excess of stoichiometric, at a temperature of between about 400° C. and about 430° C., at a pressure of between about 1 atmosphere and about 6 atmospheres, and for a time of between about 10 seconds and about 20 seconds, the weight ratio of copper chloride to potassium chloride being between about 2:1 and about 1.2:1.

9. An improved catalytic oxychlorination process for the production of perchlorethylene, which process comprises passing ethylene dichloride and above about 75% of a stoichiometric amount of chlorine or hydrogen chloride and more than a stoichiometric amount of oxygen into a reaction zone containing a fluidized bed consisting essentially of a supported catalyst in particulate fluidizable form, the supported catalyst consisting essentially of a catalytic amount of copper chloride and alkali metal chloride impregnated on a microspheroidal activated alumina support having an average particle size of between about 40 and 70 microns and a surface area of at least about 100 $m^2/g$, the weight ratio of copper chloride to alkali metal chloride being above about 1.2:1, the copper chloride calculated as $CuCl_2$, and maintaining a superficial linear velocity of the ethylene dichloride, hydrogen chloride or chlorine, and oxygen fed in the reaction zone above minimum fluidization velocity for the bed and a reaction zone temperature between about 370° C. and about 450° C. and a reaction zone pressure between about 1 atmosphere and about 15 atmospheres for a superficial reaction zone residence time of between about 5 seconds and about 30 seconds and at a mole ratio of hydrogen chloride or chlorine to ethylene dichloride sufficient to produce a reaction product containing perchloroethylene and trichloroethylene at a mole ratio of above about 5:1 with the reaction product containing less than about 150 ppm each on a perchloroethylene weight basis of 1,1,2-trichloroethane and unsym-tetrachloroethane, while still reacting above about 75 weight percent of the hydrogen chloride or chlorine.

10. A process according to claim 9 wherein the oxygen is maintained at about 20 to about 35% in excess of stoichiometric and the reaction product contains less than about 10 ppm each on a perchloroethylene weight basis of 1,1,2-chloroethane and unsym-tetrachloroethane, and wherein the catalyst mixture comprises at least above about 20% by weight of the supported catalyst.

11. An improved catalytic oxychlorination process for the production of perchloroethylene, which process comprises passing reactants consisting essentially of ethylene dichloride and hydrogen chloride with a mole ratio of hydrogen chloride to ethylene dichloride above about 1.6, and at least one member selected from the group consisting of oxygen and oxygen-containing gases, into a reaction zone with oxygen being present at about 20% to about 35% in excess of stoichiometric, the reaction zone containing a fluidized bed consisting essentially of a supported catalyst in particulate fluidizable form, the supported catalyst consisting essentially of a catalyst mixture of copper chloride and potassium chloride impregnated on a microspheroidal activated alumina support having an average particle size of between about 50 microns and about 60 microns and a surface area of between about 150 $m^2/g$ and about 250 $m^2/g$, the catalyst mixture comprising from about 25% to about 30% by weight of the supported catalyst, and the weight ratio of copper chloride to potassium chloride being between about 2:1 and about 1.2:1, the copper chloride calculated as CuCl$_2$, and maintaining a superficial linear velocity of the ethylene dichloride and other reactants fed into the reaction zone above minimum fluidization velocity for the bed and at a reaction zone temperature of between about 400° C. and about 430° C. and at a reaction zone pressure of between about 1 atmosphere and about 6 atmospheres for a superficial reaction zone residence time of between about 10 seconds and about 20 seconds and sufficient to produce a reaction product containing perchloroethylene and trichloroethylene at a mole ratio of above about 5:1 with the reaction product containing less than about 150 ppm each on a perchloroethylene weight basis of 1,1,2-trichloroethane and unsym-tetrachloroethane, while still reacting above about 75 weight percent of the hydrogen chloride.

12. A process according to claim 11 wherein the reaction product contains less than about 10 ppm each of 1,1,2-trichlorethane and unsym-tetrachloroethane on a perchloroethylene weight basis.

* * * * *